US009713656B2

(12) United States Patent
Dufrane et al.

(10) Patent No.: US 9,713,656 B2
(45) Date of Patent: Jul. 25, 2017

(54) MULTI-DIMENSIONAL BIOMATERIAL AND METHOD FOR PRODUCING THE SAME

(75) Inventors: Denis Dufrane, Wavre (BE); Christian Delloye, Wezembeek-Oppem (BE)

(73) Assignees: UNIVERSITE CATHOLIQUE DE LOUVAIN (BE); CLINIQUES UNIVERSITAIRES SAINT-LUC (BE)

( * ) Notice: Subject to any disclaimer, the term of this patent is extended or adjusted under 35 U.S.C. 154(b) by 299 days.

(21) Appl. No.: 13/376,072

(22) PCT Filed: Jun. 4, 2010

(86) PCT No.: PCT/EP2010/057847
§ 371 (c)(1),
(2), (4) Date: Dec. 2, 2011

(87) PCT Pub. No.: WO2010/139792
PCT Pub. Date: Dec. 9, 2010

(65) Prior Publication Data
US 2012/0087958 A1    Apr. 12, 2012

(30) Foreign Application Priority Data

Jun. 4, 2009 (EP) .................................... 09161976

(51) Int. Cl.
*A01N 63/00* (2006.01)
*A61L 27/38* (2006.01)
*A61L 27/36* (2006.01)
*C12N 5/0775* (2010.01)
*C12N 5/077* (2010.01)

(52) U.S. Cl.
CPC ....... *A61L 27/3821* (2013.01); *A61L 27/3608* (2013.01); *A61L 27/3817* (2013.01); *A61L 2430/02* (2013.01); *C12N 5/0653* (2013.01); *C12N 5/0667* (2013.01)

(58) Field of Classification Search
USPC ......................................... 424/400; 435/93.7
See application file for complete search history.

(56) References Cited

U.S. PATENT DOCUMENTS

| 2005/0002910 A1* | 1/2005 | Wolfinbarger et al. ...... 424/93.7 |
| 2008/0033572 A1* | 2/2008 | D'Antonio ............. A61K 35/32 623/23.51 |
| 2009/0081169 A1* | 3/2009 | Egrise .................. C12N 5/0654 424/93.7 |

FOREIGN PATENT DOCUMENTS

| AU | WO 02/062357 | * | 8/2002 | ............. A61K 35/32 |
| BE | WO 2007093431 A1 | * | 8/2007 | ........... C12N 5/0654 |
| JP | 2007/330266 | | 12/2007 | |
| WO | WO 02/062357 | | 8/2002 | |
| WO | WO 2006/042197 | | 4/2006 | |
| WO | WO 2006/062989 | | 6/2006 | |
| WO | WO 2006062989 A1 | * | 6/2006 | .......... C12N 5/0667 |
| WO | WO 2007/103442 | | 9/2007 | |
| WO | WO 2008/073331 | | 6/2008 | |
| WO | WO 2009/036279 | | 3/2009 | |
| WO | WO 2010/059565 | | 5/2010 | |

OTHER PUBLICATIONS

Loving, Nancy et al. Regenerative Stem Cell Therapy. Vet-Stem Regenerative Veterinary Medicine. Published by The Horse: Your Guide to Equine Health Care. pp. 1-2.*
Dictionary.com. "Kit". Definition retrieved from the world wide web on Feb. 24, 2014. <http://dictionary.reference.com/browse/kit?s=t>.*
Caplan, Arnold. Adult MSC for Tissue Engineering Versus Regenerative Medicine. Journal of Cellular Physiology 213. pp. 341-347. 2007.*
Hsiong (Regeneration of vascularized bone).*
Brunetti, "Transgene Expression of Green Fluorescent Protein and Germ Line Transmission in Cloned Pigs Derived from In Vitro Transfected Adult Fibroblasts," *Cloning Stem Cells*, 10(4):409-420, 2008.
Caplan, "Adult mesenchymal stem cells for tissue engineering versus regenerative medicine," 2007 J Cell Physiol 213:341-347.
Dictionary.com "kit". Definition retrieved from world wide web Feb. 24, 2014.
Dufrane et al, "In vitro evaluation of acute cytotoxicity of human chemically treated allografts," Eur Cell Mater. Jan. 10, 2010;1:52-8.
International Search Report, issued in International Patent Application No. PCT/EP2010/057847, mailed on Mar. 24, 2011.
Loving, N., et al., "Regenerative Stem Cell." Vet-Stem Regenerative Veterinary Medicine. Published by The Horse: Your guide to Equine Healthcare. pp. 1-2.
Mauney et al, "Matrix-mediated retention of adipogenic differentiation potential by human adult bone marrow-derived mesenchymal stem cells during ex vivo expansion," Biomaterials. Nov. 2005;26(31):6167-75.
Post et al., "Demonstration of the presence of independent pre-osteoblastic and pre-adipocytic cell populations in bone marrow-derived mesenchymal stem cells," *Bone*, 2008.
Qu ei al., "Osteogenic and adipogenic potential of porcine adipose mesenchymal stem cells," *Vitro Cell. Dev. Biol. Anim.*, 43:95-100, 2007.
Taipaleenmaki, et al., "Impact of Stromal Cell Composition on BMP-Induced Chonrogenic Differentiation of Mouse Bone Marrow Derived Mesenchymal Cells," Experimental Cell Research 314 (2008), pp. 2400-2410.

(Continued)

*Primary Examiner* — Scott Long
*Assistant Examiner* — Nghi Nguyen
(74) *Attorney, Agent, or Firm* — Norton Rose Fulbright US LLP

(57) ABSTRACT

Biomaterial having a multi-dimensional structure and comprising demineralized bone matrix dispersed within differentiated mesenchymal stem cells (MSCs) tissue, wherein MSCs are adipose tissue-derived stem cells. Method for producing this biomaterial comprising incubating MSCS in osteoblastic and/or chondrongenic medium in presence of demineralized bone matrix. Use of this biomaterial for alleviating or treating a bone or cartilage defect, supporting or correcting a congenital or acquired abnormality, supporting a bon or articular bone replacement following surgery or trauma, and/or supporting a musculoskeletal implant.

13 Claims, 6 Drawing Sheets

(56) References Cited

OTHER PUBLICATIONS

Tsiridis et al., "In vitro proliferation and differentiation of human mesenchymal stem cells on hydroxyapatite versus human demineralised bone matrix with and without osteogenic protein-1," *Expert Opinion on Biological Therapy*, 9(1):19, 2009.

Zhou et al., "Demineralized bone promotes chrondrocyte or osteoblast differentiation of human marrow stromal cells cultured in collagen sponges," *Cell and Tissue Banking*, 6(1):33-44, 2005.

Duque, G. "Will Reducing Adipogenesis in Bone Increase Bone Mass?: PPARγ2 as a Key Target in the Treatment of Age-Related Bone Loss" Drug News Perspect (2003) vol. 16(6), pp. 341-346.

Saran et al., Review: Role of angiogenesis in bone repair, Archives of Biochemistry and Biophysics, vol. 561, p. 109-117, 2014.

Shelby, J. et al: "A-42: Use of Human Adult Derived Adipose Stem Cells and Demineralized Bone Matrix to Regenerate Bone Tissue In Vivo" American Association of Tissue Banks, 29th Annual Meeting (Sep. 17-20, 2005), Hollywood, Florida.

Tavian et al. "The Vascular Wall as a Source of Stem Cells," Ann. N.Y. Acad. SCi. 1044:41-50 (2005).

Wang Zhen, X-ray diagnostics, 1994, Heibei Education Press, published on Jun. 1994 (with English translation of relevant passage).

Yu Yue, Fundamental and Clinic Research of Stem cells, pp. 175-176, published on Dec. 31, 2008, University of Science and Technology of China Press, HE FEI, China (with English translation of relevant passage).

Zhao et al., "Crosslinked three-dimensional demineralized bone matrix for the adipose-derived stromal cell proliferation and differentiation" Tissue engineering, Part A, 2009, 15(1):13-21.

\* cited by examiner

HUMAN AMSC: MONOLAYER VERSUS MULTI-DIMENSIONAL CELLULAR STRUCTURE: USE OF HMAN SERUM FOR OSTEOGENIC DIFFERENTIATION.

MULTI-DIMENSIONAL BIOMATERIAL AND METHOD FOR PRODUCING THE SAME

This application is a national phase application under 35 U.S.C. §371 of International Application No. PCT/EP2010/057847 filed 4 Jun. 2010, which claims priority to European Application No. 09161976.7 filed 4 Jun. 2009. The entire text of each of the above-referenced disclosures is specifically incorporated herein by reference without disclaimer.

FIELD OF THE INVENTION

This invention is directed to the field of mesenchymal stem cells and their differentiation for the production of multi-dimensional tissues or biomaterials or matrices. The products of the invention may be useful in rheumatology, in tissue reconstruction, and/or in surgery, especially traumatology, orthopaedic, plastic and maxillifacial surgery. Especially, the products of the invention may be useful in bone or cartilage repair or replacement.

BACKGROUND OF THE INVENTION

Tissue engineering is a growing field where new materials are being developed for implantation into the body. One important area involves bone graft materials to replace areas of bone lost to trauma or disease (as e.g. tumor resection). Traditionally, graft material may be harvested from the bone of the individual receiving the graft material. However, this requires an additional surgery and additional recovery. Bone also may be taken from others, or even cadavers, but this introduces biocompatibility problems as well as the risk of disease transfer.

Researches have been conducted in the field of stem cell differentiation for producing tissues. For example, WO2007/103442 discloses a composition comprising a silk scaffold and an adult stem cell, wherein said adult stem cell is an adipose-derived stem cell.

TECHNICAL ISSUE

However, the production of multi-dimensional tissues for use in bone graft or bone reinforcement or bone reconstruction remains a real technical issue. The same issue also remains in cartilage reconstruction, or for alleviation of cartilage defects.

There is thus still a need in the art for tissue engineered materials that are fully biocompatible and provide appropriate mechanical features for the designated applications.

SUMMARY OF THE INVENTION

This invention relates to a natural human osteoinductive biomaterial having a multi-dimensional structure and comprising differentiated mesenchymal stem cells (MSCs) tissue and demineralised bone matrix (DBM), wherein said demineralised bone matrix is dispersed within the differentiated MSCs tissue.

The MSC used in order to make the differentiated MSCs tissue may be of human or animal origin.

According to a first embodiment, the MSCs have been isolated from adipose tissue, and are hereinafter referred to as adipose tissue mesenchymal stem cells (AMSCs).

According to another embodiment, the MSCs have been isolated from bone marrow and are hereinafter referred to as Bone-marrow stem cells (BMSCs) preferably, the MSCs included in the biomaterial of the invention are late passaged adipose tissue-derived stem cells.

The biomaterial of the invention is intended to be implanted in a human or animal body. The implanted biomaterial may be of autologous origin, or allogenic. The biomaterial of the invention may be implantable in a bone a cartilage area. The biomaterial of the invention may be implanted in irregular areas of the human or animal body.

The biomaterial of the invention is biocompatible.

Typically, the biomaterial of the invention is homogeneous, which means that the structure and/or constitution of the biomaterial are similar throughout the whole tissue. Typically, the biomaterial of the invention has desirable handling and mechanical characteristics required for implantation in the native disease area.

According to a particular embodiment, the biomaterial of the invention can be held with a surgical instrument without being torn up.

In an embodiment of the invention, the biomaterial does not include any cohesiveness agent or binding agent.

According to a preferred embodiment, the biomaterial according to the invention is three-dimensional. In this embodiment, the biomaterial of the invention may form a thick film having a thickness of at least 1 mm. The size of the biomaterial may be suited as convenient for the use. In another embodiment, the biomaterial forms a scaffold: thus, the biomaterial of the invention does not need the use of any further synthetic scaffold.

According to another embodiment, the biomaterial of the invention may form a thin film of less than 1 mm. In this embodiment, the biomaterial is said two-dimensional.

According to a first embodiment, the biomaterial of the invention has the same properties as a real bone with osteocalcin expression and mineralization properties, i.e. it comprises osseous cells and an interconnective tissue. According to a particular embodiment, the biomaterial of the invention comprises osseous cells (also called osteocyte-like cells) and collagen, preferably calcified and mineralized collagen, an osseous matrix, and a mineral coating onto the osseous cells, the coating being organized phosphocalcic crystals. Typically, the biomaterial of the invention has a porosity close to that of natural bone.

According to a second embodiment, the biomaterial of the invention has the same properties as a real cartilage, i.e. it comprises chondrocytes, an extracellular matrix comprising collagen and proteoglycans.

The recolonization properties of the biomaterial of the invention may depend on the environment where the biomaterial is implanted: the biomaterial of the invention may be recolonizable when placed in an osseous environment, and may be unrecolonizable when placed in a non-osseous environment.

The biomaterial of the invention is such that the differentiation of the cells of the biomaterial has reached an end point, and the phenotype of the biomaterial will remain unchanged when implanted. The implant of the invention may be multi-layered, i.e. it comprises at least two layers of biomaterial, possibly sutured or fixed one to another by any suitable means, such as for example a surgical glue or any suitable fixation means.

Typically, the biomaterial of the invention includes a demineralised bone matrix in the form of particles have a mean diameter of 50-2500 µm; in a first embodiment, the particles have a mean diameter of 50-125 µm; in a second embodiment the particles have a mean diameter of 125-200 µm; in a third embodiment the particles have a mean diameter of 500 to 1000 µm. Typically, the demineralised bone matrix is issued from donors aged less than 40 years old. According to an embodiment, the demineralization rate of the bone matrix is of 90-99%, preferably 95-98%, and even more preferably about 97%. This demineralization rate advantageously results from a process using HCl 0.6N during three hours. According to a specific embodiment, the demineralised bone matrix is sterilized.

According to a particular embodiment, the demineralised bone matrix is provided by University Tissue Bank (Cliniques universitaires Saint-Luc, Brussels, Belgium).

This invention also relates to a method for producing a multi-dimensional biomaterial comprising incubating MSCs in osteoblastic and/or chondrogenic media during 15-25 days and then adding demineralised bone matrix in said media and maintaining incubation for an additional period of 15-30 days, preferably 15-25 days, more preferably 20 days; during the additional period, preferably replacing the media every 2 days without removal of the demineralised bone matrix.

Incubating MSCs before adding demineralised bone matrix is a key step of the method of the invention. Such a step is necessary for allowing the differentiation of the MSCs into chondrogenic cells and/or osteoblastic cells. In addition, this step is necessary for obtaining a 3 D bone like structure.

According to a preferred embodiment, the MSC are late passaged adipose tissue mesenchymal stem cells.

According to one embodiment, 1 to 20 mg of demineralised bone matrix per ml of medium is added. According to a preferred embodiment, 1 to 10 mg of demineralised bone matrix per ml of medium is added.

Most preferably, 5 to 10 mg of demineralised bone matrix per ml of medium is added. Said quantity of demineralised bone matrix is the optimal concentration for providing a 3D bone-like structure of the biomaterial.

According to one embodiment, all media are free of animal proteins.

According to a second embodiment, the differentiation medium contains human serum. Advantageously, the differentiation medium does not contain any animal serum, preferably it contains no other serum than human serum.

The invention also relates to a multi-dimensional biomaterial obtainable by the method according to the invention. The biomaterial obtainable by the method of the invention is intended to be implanted in a human or animal body. The implanted biomaterial may be of autologous origin, or allogenic. The biomaterial of the invention may be implantable in a bone a cartilage area. This biomaterial may be implanted in irregular areas of the human or animal body.

The biomaterial obtainable by the method of the invention is biocompatible.

This biomaterial is homogeneous, which means that the structure and/or constitution of the biomaterial are similar throughout the whole tissue. Preferably, this biomaterial has desirable handling and mechanical characteristics required for implantation in the native disease area. Typically, the biomaterial obtainable by the method of the invention can be held with a surgical instrument without being torn up.

In an embodiment of the invention, the biomaterial does not include any cohesiveness agent or binding agent.

In another embodiment, the biomaterial obtainable by the method of the invention is three-dimensional. In this embodiment, the biomaterial may form a thick film having a thickness of at least 1 mm. The size of the biomaterial may be suited as convenient for the use. In another embodiment, the biomaterial forms a scaffold: thus, the he biomaterial obtainable by the method of the invention does not need the use of any further synthetic scaffold.

In still another embodiment, the biomaterial obtainable by the method of the invention may form a thin film of less than 1 mm. In this embodiment, the biomaterial is two-dimensional.

According to a first embodiment, the biomaterial obtainable by the method of the invention has the same properties than a real bone with respect of the osteocalcin expression and mineralization property, i.e. it comprises osseous cells and an interconnective tissue. In one embodiment, this biomaterial comprises osseous cells (also called osteocyte-like cells) and collagen, preferably calcified and mineralized collagen, an osseous matrix, and a mineral coating onto the osseous cells, the coating being organized phosphocalcic crystals. Typically, the biomaterial has a porosity close to that of natural bone.

According to a second embodiment, the biomaterial obtainable by the method of the invention has the same properties as a real cartilage, i.e. it comprises chondrocytes, an extracellular matrix comprising collagen and proteoglycans.

The biomaterial obtainable by the method of the invention is such that the differentiation of the cells of the biomaterial has reached an end point, and the phenotype of the biomaterial will remain unchanged when implanted. The implant of the invention may be multi-layered, i.e. it comprises at least two layers of biomaterial, possibly sutured or fixed one to another by any suitable means, such as for example a surgical glue or any suitable fixation means.

The biomaterial obtainable by the method of the invention includes a demineralised bone matrix in the form of particles having a mean diameter of 50-2500 µm; in a first embodiment, the particles have a mean diameter of 50-125 µm; in a second embodiment the particles have a mean diameter of 125-200 µm; in a third embodiment the particles have a mean diameter of 500 to 1000 µm. Typically, the demineralised bone matrix is issued from donors aged less than 40 years old. According to an embodiment, the demineralization rate of the bone matrix is of 90-99%, preferably 95-98%, and even more preferably about 97%. This demineralization rate advantageously results from a process using HCl 0.6N during three hours. According to a preferred embodiment, the demineralised bone matrix is sterilized.

Typically, the demineralised bone matrix is provided by University Tissue Bank (Cliniques universitaires Saint-Luc, Brussels, Belgium).

The invention relates to any use of the biomaterial of the invention, as a medical device or included into a medical device, or in a pharmaceutical composition.

The invention also relates to a kit, comprising a medical device comprising the biomaterial of the invention, and a suitable fixation means, such as for example a surgical glue, or a tissue-glue, or any adhesive composition which is biocompatible, non-toxic for surgical use, and possibly bioresorbable and, in particular for joining biological tissues to each other or to an implanted biomaterial.

The invention further relates to a kit, comprising the biomaterial of the invention, and a suitable fixation means, such as for example a surgical glue, or a tissue-glue, or any adhesive composition which is biocompatible, non-toxic for surgical use, and possibly bioresorbable and, in particular for joining biological tissues to each other or to an implanted biomaterial.

In another aspect, the invention relates to the biomaterial according to the invention for use in a method for alleviating or treating a bone or cartilage defect This invention also relates to a method of alleviating or treating a bone or cartilage defect in a mammal, said method comprising administering to said mammal having a bone or cartilage defect a therapeutically effective amount of a biomaterial as herein described.

The biomaterial is used in a therapeutically effective amount for alleviating or treating a bone or cartilage defect in a mammal.

Non limiting example of bone or cartilage defect are bone fracture, born frailty, loss of bone mineral density, arthritis, osteoporosis, osteomalacia, osteopenia, bone cancer, Paget's disease, sclerotic lesions, infiltrative disorders of bone, metabolic bone loss.

The invention also relates to the use of the biomaterial in orthopedics, especially in maxillofacial or plastic surgery. The biomaterial of the invention may also be used in rheumatology.

The invention further relates to a method of using the biomaterial of the invention for supporting or correcting congenital or acquired abnormalities of the joints, craniofacial-maxillary bones, orthodontic procedures, bone or articular bone replacement following surgery, trauma or other congenital or acquired abnormalities, and for supporting other musculoskeletal implants, particularly artificial and synthetic implants.

In another aspect, the invention relates to the biomaterial of the invention for use for filling a bone cavity with the human or animal body.

In still another aspect, the invention relate to the biomaterial of the invention for use for reconstructive or aesthetic surgery. The biomaterial of the invention may be autologous or allogeneic. It may be used in tissue grafting.

The invention further relates to a method of filling a cavity within the human or animal body, said method comprising the step of administering the biomaterial of the invention.

The biomaterial of the invention may be used as an allogeneic implant or as an autologous implant.

The biomaterial is also advantageous in that it is non-immunogenic and in that it has an immunomodulating effect: surprisingly, in the biomaterial of the invention, the immunomodulating properties of undifferentiated MSC are retained, resulting in that the implantation of the biomaterial of the invention within the human or animal body does not result in any inflammatory reaction: on the contrary, the presence of the biomaterial alleviates inflammation on site of implantation.

The biomaterial of the invention is thus especially suitable for the treatment of arthritis, especially of inflammatory arthritis, as an alternative to anti-inflammatory pharmaceuticals or as a means to reduce the amount of anti-inflammatory pharmaceuticals needed in a patient suffering from the consequences of said inflammation.

The biomaterial of the invention is further advantageous for stimulating angiogenesis. Indeed, the MSCs of the biomaterial release vascular endothelial growth factor (VEGF) which stimulates the growth of new blood vessel. Such an aspect of the invention is highly promising since it provides optimal conditions for bone or cartilage formation.

DEFINITIONS

In the meaning of this invention, the term "tissue" refers to a collection of interconnected cells that perform a similar function within a native human tissue.

In the meaning of this invention, the term "mesenchymal stem cells" or MSCs, are multipotent stem cells that can differentiate into a variety of cell types.

"Adipose" refers to any fat tissue. The adipose tissue may be brown, yellow or white adipose tissue. Preferably, the adipose tissue is subcutaneous white adipose tissue. Adipose tissue includes adipocytes and stroma. Adipose tissue may be found throughout the body of an animal. For example, in mammals, adipose tissue is present in the omentum, bone marrow, subcutaneous space, fat pads (e.g., scapular or infrapatellar fat pads), and surrounding most organs. Cells obtained from adipose tissue may comprise a primary cell culture or a progenitor cell line. The adipose tissue may be from any organism having fat tissue.

The term "adipose tissue-derived cell" refers to a cell that originates from adipose tissue. The initial cell population isolated from adipose tissue is a heterogenous cell population including, but not limited to stromal vascular fraction (SVF) cells.

As used herein, the term "adipose tissue mesenchymal stem cells" (AMSCs) refer to stromal cells that originate from adipose tissue which can serve as precursors to a variety of different cell types such as, but not limited to, adipocytes, osteocytes, chondrocytes.

As used herein, the term "late passaged adipose tissue mesenchymal stem cells" refers to a cell exhibiting a less immunogenic characteristic when compared to an earlier passaged cell. The immunogenicity of an adipose tissue-derived stromal cell corresponds to the number of passages. Preferably, the cell has been passaged up to at least the fourth passage, more preferably, the cell has been passaged up to at least the sixth passage, and most preferably, the cell has been passaged up to at least the eight passage.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, a "graft" refers to a cell, tissue or organ that is implanted into an individual, typically to replace, correct or otherwise overcome a defect. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "tissue grafting" and "tissue reconstructing" both refer to implanting a graft into an individual to treat or alleviate a tissue defect, such as for example a bone defect or a cartilage defect.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, "bone defect" refers to bone that is broken, fractured, missing portions or otherwise damaged. Such damage may be due to congenital anomaly, disease, disease treatment, trauma or osseous infection, and may be acute or chronic. For instance, bone loss may occur as a result of tumor resection, thus resulting in a bone defect. Non-limiting examples of bone defects include: bone fractures, bone/spinal deformation, osteosarcoma, myeloma, bone dysplasia, scoliosis, osteroporosis, osteomalacia, rickets, fibrous osteitis, fibrous dysplasia, renal bone dystrophy, and Paget's disease of bone.

As used herein, "cartilage defect" refers to cartilage tissue that is missing, reduced in quantity or otherwise damaged. A cartilage tissue defect may result from a congenital anomaly, disease, disease treatment, or trauma, and may be acute or chronic (osteoarthritis).

As used herein, the term "osteoblastic and/or chondrogenic media" is meant to refer to a culture medium that promotes growth and differentiation of osteoblastic and/or chondrogenic cells.

Advantageously, osteogenesis is induced by supplementing a standard medium with Human or animal (preferably foetal calf or bovine serum (FCS, FBS)) Serum, dexamethasone, sodium ascorbate, sodium dihydrophosphate, penicillin, and streptomycin. Cells are maintained in osteogenic culture with medium replaced every 2 days.

In a preferred embodiment, the osteoblastic medium is a standard medium, preferably DMEM, supplemented with 10% v/v of Human Serum, 1 µM of dexamethasone, 50 µg/ml of sodium ascorbate, 36 mg/ml of sodium dihydrophosphate, 100 U/ml of penicillin, and 100 µg/ml of streptomycin.

Chondrogenesis is advantageously induced by supplementing a standard medium with Human or animal (preferably foetal calf or bovine serum (FCS, FBS)) Serum, dexamethasone, TGF-B3, L-proline, sodium ascorbate, sodium dihydrophosphate, sodium pyruvate, ITS (Insulin-Transferrin-Selenium, e.g. from insulin-transferrin-sodium selenite media supplement lyophilized powder available from Sigma), penicillin, and streptomycin.

A preferred chondrogenic medium is a standard medium, preferably DMEM, supplemented with 10% v/v of Human Serum, 1 µM of dexamethasone, 10 ng of TGF-B3, 40 µg/ml of L-proline, 50 µg/ml of sodium ascorbate, 36 mg/ml of sodium dihydrophosphate, 100 µg/ml of sodium pyruvate, 100 µl/ml of ITS (Insulin-Transferrin-Selenium, e.g. from insulin-transferrin-sodium selenite media supplement lyophilized powder available from Sigma), 100 U/ml of penicillin, and 100 µg/ml of streptomycin.

Suitable standard media for both the osteogenic and chondrogenic media include but are not limited to DMEM, EMEM, RPMI, and GMEM, DMEM being the preferred standard medium.

As used herein, "scaffold" refers to a structure, including in the form of, but are not limited to, films (e.g. a form with two-dimensions substantially greater than the third dimension), ribbons, cords, sheets, flat discs, cylinders, spheres, 3-dimensional amorphous shapes, etc.

EXAMPLES

Example 1

Figure 1:
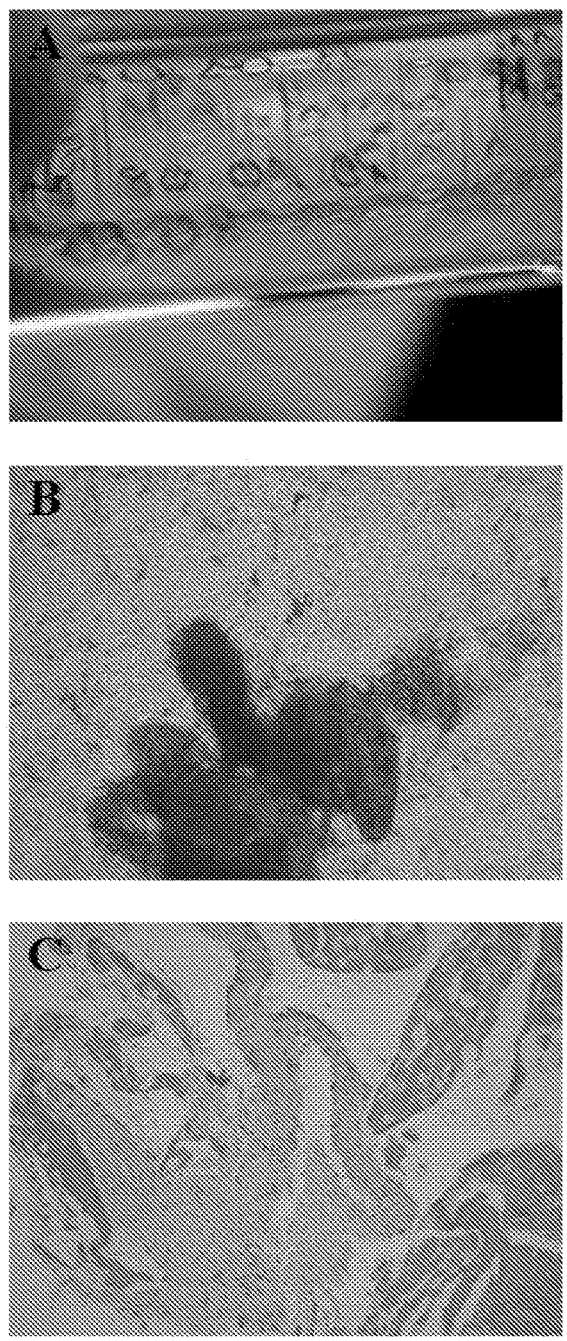
FIG. 1 shows human AMSCs differentiation in osteogenic medium supplemented with Human serum and DBM. A multi-layer structure (A) with tissue retraction and inter-connective tissue (B) was found by staining with Trichrom Masson's staining (C).

Preparation of the Multi Dimensional Biomaterial According to the Invention

Animals Source for AMSCs in Pre-Clinical Model

Green Fluorescent transgenic pigs were used as donor for bone marrow and adipocytes stem cells (Brunetti D, Cloning Stem Ceils, eupb 2008). Animals were housed according to the guidelines of the Belgian Ministry of Agriculture and Animal Care. All procedures were approved by the local Ethics Committee for Animal Care of the Université catholique de Louvain.

Source for AMSCs of Animal Origin

The collagenase (0.075 g) is reconstituted in Hank's Balanced Salt Solution (with calcium ions) and stored at 2-8° C. prior digestion. Fatty tissues (a mean of 15 g) were washed three times with NaCl 0.009% and were cut in a Petri-dish to remove vessels and fibrous connective tissue. The fat is weighed prior to digestion and is transferred in a 50-ml Flacon tube containing the enzyme. The tissue is placed in a shaking water bath at 37° C. with continuous agitation for 60 minutes. After digestion, the collagenase is inactivated in DMEM (500 ml) supplemented with 50 ml of Human serum, L-glutamin (5 ml) and 5 ml antibiotics (penicillin/streptomycin). Collected tissue is centrifuged for 10 min at 1500 rpm at room temperature (20-25° C.). The supernatant, containing mature adipocytes, is aspirated. The pellet is re-suspended in 20 ml of proliferation medium (MP) made of DMEM supplemented with 10% of Human Serum and antibiotics (100 U/ml of penicillin and 100 µg/ml of streptomycin) and filtered through a 500 µm mesh-screen. The collected tissue (after filtration) is centrifuged for 10 min at 1500 rpm at room temperature (20-25° C.) and the pellet is re-suspended in the MP and is identified as the Stromal Vascular Fraction (SVF) cells. This initial passage of the primary cells was referred to as passage 0 (P0). After 24-48 hours of incubation at 37° C. at 5% $CO_2$, the cultures were washed with PBS and maintained in the MP up to P4 (fourth passage) and then differentiated in specific media (see below).

Source for AMSCs of Human Origin

Human fatty tissue (small pieces of subcutaneous fatty tissue, 1-2 g, n=4) was removed during routine surgery (abdominal and orthopaedic surgery), preserved in a cold 4° C. physiological solution up to the laboratory for processing. Human fatty digestion was processed as previously described for pig fatty tissue processing. After digestion, human AMSCs were cultivated in MP and differentiated in specific media (see below for exact composition) supplemented with (i) Foetal Bovine Serum (10% v/v) or (ii) Human Serum (10% v/v).

It was observed that the AMSC differentiated in both differentiation media containing FBS and differentiation media containing Human Serum.

Source for Demineralized Bone Matrix

Human demineralized bone matrix was provided by the University Tissue Bank (Cliniques universitaires Saint-Luc, Brussels, Belgium), and produced from multi-organ human donors. Diaphysis of femoral or tibial bone is cut and pound in particles below 1000 µm for demineralization treatment (see below).

Human DBM is performed by grinding cortical bones from selected human donors. Firstly, human bone tissue is defatted by Acetone (99%) bath during an overnight and followed by washing in demineralised water during 2 hours. Decalcification is performed by immersion in HCL 0.6 N during 3 hours (20 ml solution per gram of bone) under agitation at room temperature. Then, demineralized bone powder is rinsed with demineralised water during 2 hours and the pH is controlled. If the pH is too acid, DBM is buffered with Phosphate solution at O.1 M under agitation. Finally, DBM is dried and weight. The DBM is sterilized with 25 kGray by Gamma irradiation at frozen temperature.

Stem Cells Differentiation and Characterization

Adipogenesis

Confluent cultures of AMSCs were induced to undergo adipogenesis by replacing the MP with adipocyte induction medium composed of Iscove modified Duibecco's Medium (IMDM) supplemented with 20% Human Serum, L-glutamine (5 ml), bovine insulin (5 µg/ml), indomethacine (50 µM), 3-isobutyl-1-methyl-xanthine (IBMX, 0.5 mM), dexamethasone (1 µM) and penicillin 100 U/ml and streptomycin 100 µg/ml (Mauney J R, Biomaterials 2005, vol 26: 6167). Cells were maintained in adipogenic culture with media replaced every 2 days. Cultures were rinsed with PBS and fixed in formalin solution and adipocyte differentiation was determined by staining of neutral lipids with oil red.

Osteogenesis

Figure 3:
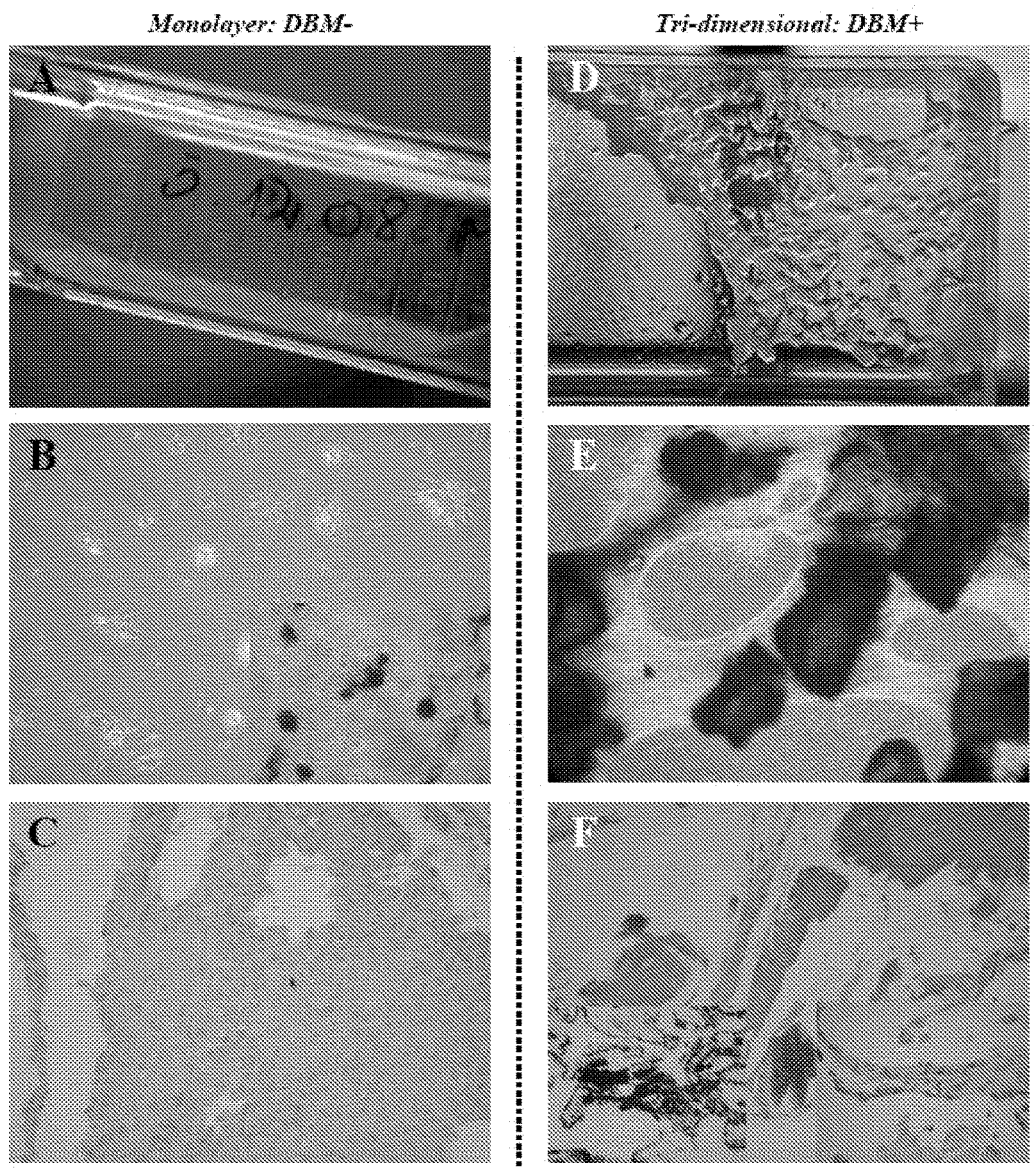
FIG. 3 shows human AMSCs differentiation in osteogenic medium without (A, B, C) and with (D, E, F) DBM. A monolayer structure (A) made of individual bone nodules (Alizarin Red staining, B) and intra-nodule collagen tissue (C) was developed in osteogenic medium without DBM. In contrast, cellular tissue retraction (D) with inter-connective tissue (E) made of mineralized collagen (F, Von Kossa staining in black: left rectangle) with osteocalcin-expressing cells (F, right rectangle).
Figure 4:
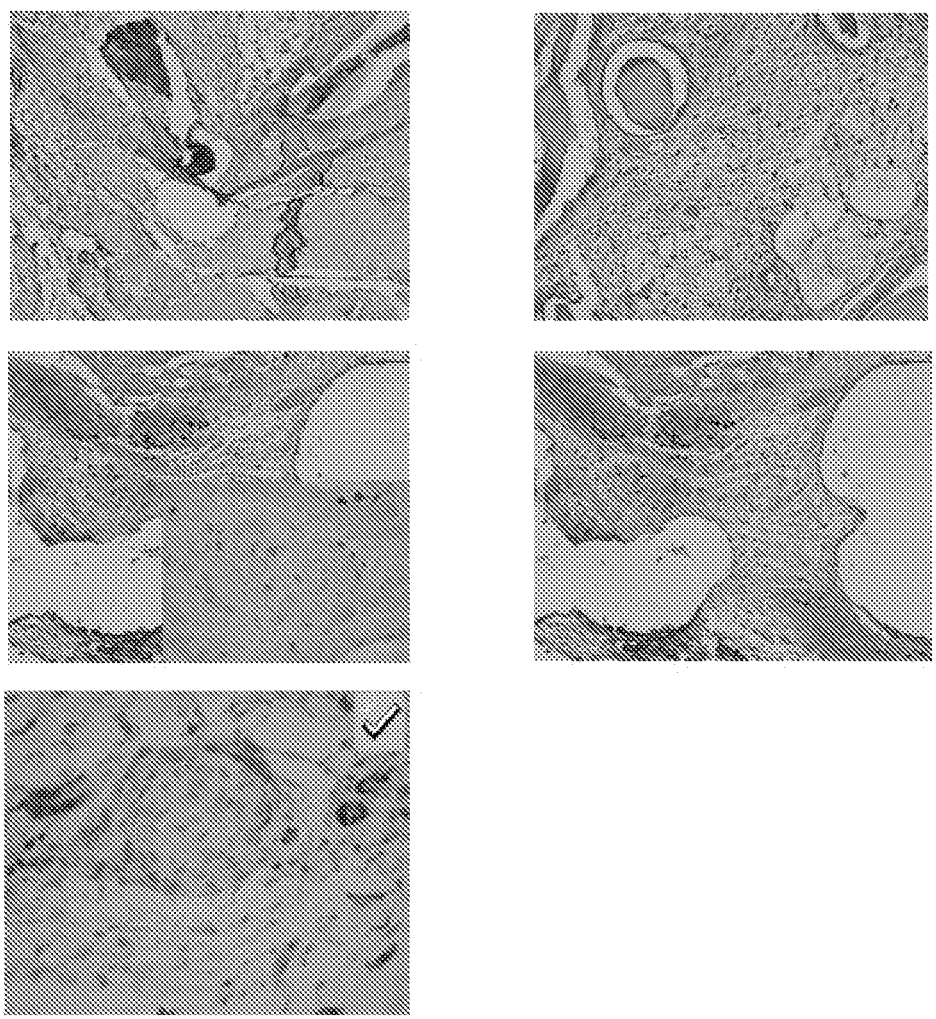
FIG. 4 shows BM-MSCs and AMSCs viability alter 60 days post-implantation in para-vertebral muscles of nude rats. Mesenchymal stem cells were detected by immunohistochemistry for GFP and osteocalcin antibody. In case of bone alone implantation, no expression of GFP and osteocalcin staining cells were found. In case of composite grafts made of "MSC—human bone graft", GFP and osteocalcin cells were detected.

Confluent cultures of AMSCs were induced to undergo osteogenesis using a osteogenic medium obtained by supplementing DMEM with Human Serum (10% v/v), dexamethasone (1 µM), sodium ascorbate (50 µg/ml), sodium dihydrophosphate (36 mg/ml), penicillin (100 U/ml), and streptomycin (100 µg/ml) (see FIG. 3-A,B,C). Cells were maintained in osteogenic culture with media replaced every 2 days. Cultures were rinsed with PBS and fixed in 70% ethanol and osteogenic differentiation was determined by staining for calcium phosphate with Alizarin red. In addition, immunohistochemistry for osteocalcin and von Kossa stainings were performed to confirm the "bone" phenotype (see FIG. 4).

Chondrogenesis

Confluent cultures of AMSCs were induced to undergo chondrogenesis using a chondrogenic medium obtained by supplementing DMEM with Human Serum (10% v/v), dexamethasone (1 µM), TGF-B3 (10 ng), L-proline (40 µg/ml), sodium ascorbate (50 µg/ml), sodium dihydrophosphate (36 mg/ml), sodium pyruvate (100 µg/ml), ITS (Insulin-Transferrin-Selenium, e.g. from insulin-transferrin-sodium selenite media supplement lyophilized powder available from Sigma) (100 µg/ml), penicillin (100 U/ml), and streptomycin (100 µg/ml) (Taipaleenmäki H, Experimental Cell Research 2008 vol 314: 2400). Cells were maintained in chondrogenic culture with media replaced every 2 days.

Impact of Differentiation Media (Osteogenic and Chondrogenic on AMSCs) Growth.

Cell and Culture Conditions.

AMSCs were grown in proliferation medium (MP) and maintained at 37° C. (95% air and 5% $CO_2$) until about 85-90% confluence. The medium was changed every 2 days. To suspend cells for cytotoxicity assay, cells were detached from the culture flask with a 0.25% trypsin-EDTA mixture for 10 min at 37° C. and were resuspended in the culture medium. Cells were seeded in 96-well microplates for MTS (3-[4,5dimethylthiazol-2yl]-5-[3-carboxymethoxyphenyl]-2-[4-sulfophenyl]-2H-tetrazolium bromide) at a density of 1×104 cells/well. They were grown near confluency at 96 hours at 37° C. prior exposition to different tested media: (i) MP, (ii) osteogenic medium, and (iii) chondrogenic medium for 5 days.

MTS Assay.

After 24 hours of extract-cell contact, 20 µl of "Cell titer 96® AQ$_{ueous}$One Solution Cell Proliferation Assay" (Promega, Madison, Wis.) was added directly to each well containing 100 µl of extract medium. Cells were incubated for 3 hours at 37° C. The absorbance was measured at 492 nm using a microtiter plate spectrophotometer (Multiskan Ex, Labsystems, Brussels, Belgium). The reference wavelength was 690 nm. The optical density difference OD=$OD_{492nm}$−$OD_{690nm}$ was estimated.

It was observed that differentiation occurred only when using specific differentiation media.

Development of Multi-Dimensional Structure

After 15-20 days of incubation of AMSC (subculture Passage 4) in specific media (osteogenic or chondrogenic), demineralized bone matrix (DBM) was supplemented to osteogenic and chondrogenic media resulting in a multi-dimensional structure (1 mg of DBM/ml of differentiated media) for an additional period of 20 days. The media is replaced every 2 days without removal of DBM.

Figure 2:
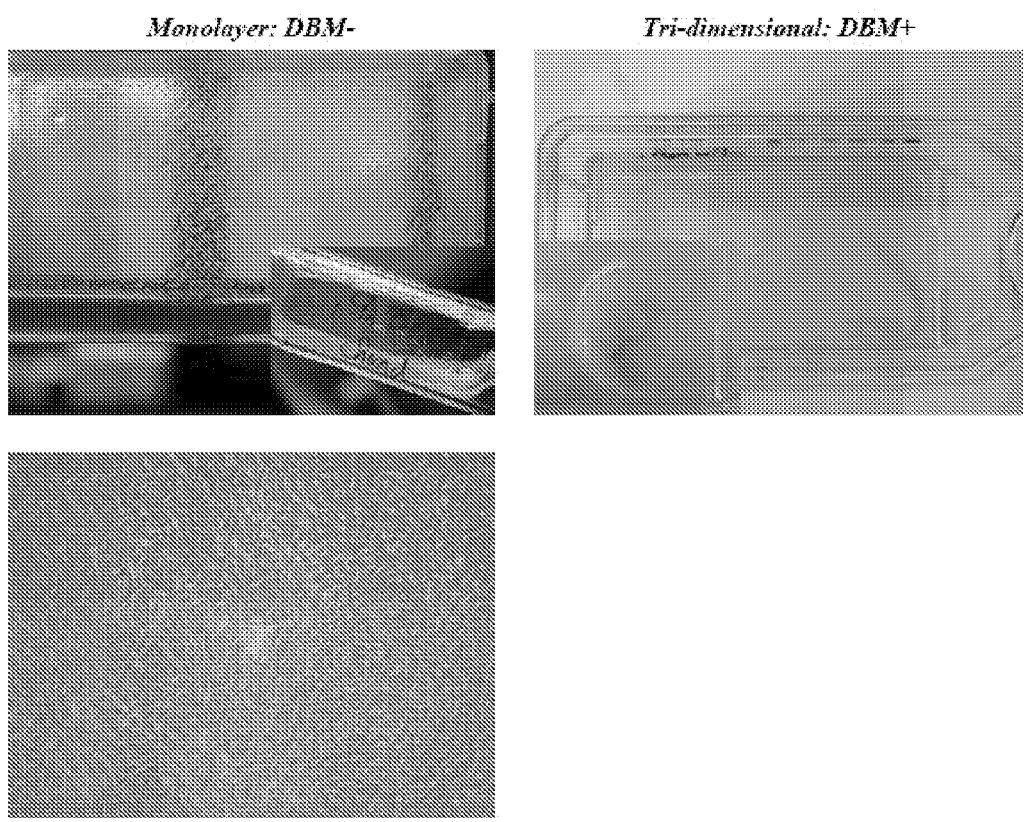
FIG. 2 shows AMSCs differentiation in chondrogenic medium without (Left) and with (Right) DBM. A monolayer structure with confluent cell was developed in chondrogenic medium without DBM. In contrast, a multilayer structure obtained by cellular tissue retraction was composed by chondrogenic-like matrix stained by Alcian blue.

At the end of differentiation, cultures were rinsed with PBS and fixed in formalin solution for bone and chondrogenic characterization by histology for osteocalcin, Alcian Blue and Giemsa stainings (FIG. 2-C,D,E, FIG. 3-D,E,F).

Cellular pellets were fixed in 4% paraformaldehyde for overnight. Serial sections (5 µm thick) were mounted on glass slides with demineralized water, dried for 12 hours at 37° C. and processed by immuno-classical detection or histochemistry. Endogenous peroxidase activity was blocked by placing sections in hydrogen peroxide (0.3% $H_2O_2$) for 30 min. After washing in Tris-Triton buffered saline (TBS-0.05M, 0.05%, pH=7.4), slides were incubated for 30 minutes at room temperature with normal goat serum (1:10; BIOSYS, Boussens, France) and overnight with a primary antibody for staining osteocalcin (anti-osteocalcin monoclonal mouse antibody; ABCAM, Cambridge, UK) at a dilution of 1:100. After washing with Tris-TBS, the slides were incubated for 1 hour with secondary anti-mouse IgG for immunoperoxydase detection.

Collagen structure was studied by Masson's Trichrom on each sample for all types of un/differentiated cells. Fibroblastic cells incubated in proliferation and differentiation (osteogenic, chondrogenic and adipogenic) media served as negative control.

Proteoglycan-secreting chondrocytes were stained with Alcian Blue and Giemsa stainings.

AMSCs were stained with saturating amounts of monoclonal CD9O antibody conjugated with phycoerythrin (PE). At least 15,000 events were analyzed by flow cytometry (FACScan, BD Biosciences) with Celiquest software.

Figure 5:
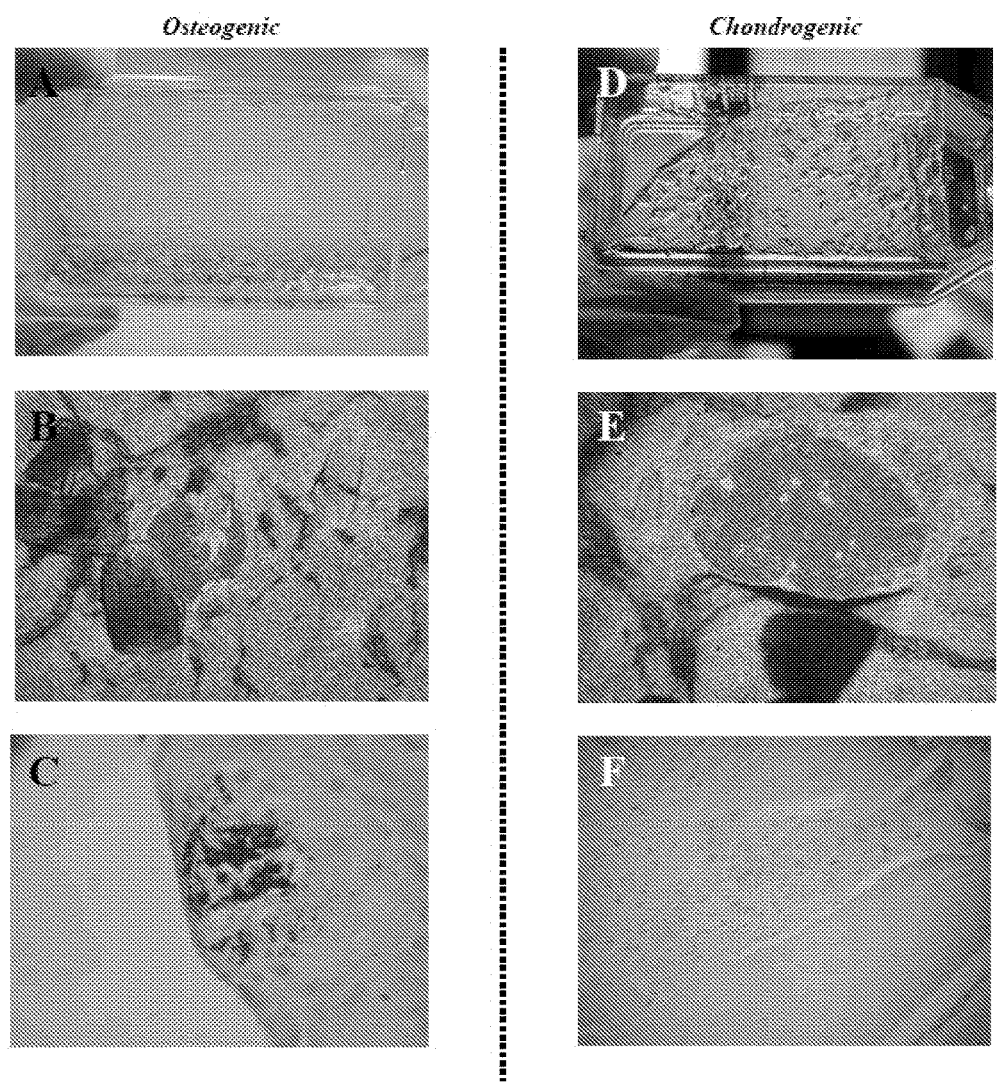
FIG. 5 shows the development of multi-dimensional structures for AMSCs incubated in osteogenic (A-C) and chondrogenic (E-F) medium supplemented with DBM. Tissue retraction (A, D), DBM inter-connexion (B, E) and expression of Osteocalcin© and proteoglycan (F) proteins.

In both osteogenic and chondrogenic differentiation media, supplemented DBM induced the development of a three-dimensional structure by a cellular construction, collagen synthesis and regroupment of demineralized bone matrix particles (see FIG. 5 A-E). Microscopically, osteocalcin expression and proteoglycan secretion were revealed in osteogenic (FIG. 5C) and chondrogenic (FIG. 5F) conditions, respectively.

In Vivo Implantation and Histology Analysis

Osteoblastic differentiated GFP-pig AMSCs were seeded on a human treated/decellularized bone matrix (Dufrane D, Eur Cell Mater, vol 1: 52, 2001) provided by the University Tissue Bank (University clinical hospital Saint-Luc, Brussels, Belgium). The composite graft was implanted subcutaneously in para-vertebral region of nude rats (2 implants/recipient and n=1O) (male, 6-8 weeks old). After 60 days, animals were sacrificed and implants were explanted for immunohistochemistry processing. Implants were then decalcified in HCL, processed and embedded in parrafin and sectioned (5 µm). Masson's Trichrom and immunohistochemistry for osteocalcin and "Green Fluorescent Protein" (monoclonal antibody) were then performed.

Example 2

Potential of Multidimensional Bone-Like Graft from Adipose Mesenchymal Stem Cells Materials and Methods Pig and Human AMSC Isolations For the purpose of those experiments, the pig and human AMSC isolations were carried out as disclosed in example 1.

Angiogenesis Potential of AMSCs

In Vitro

To assess in vitro the proangiogenic capacities of stem cells in normoxic and hypoxic conditions, porcine Bone Marrow-MSC and Adipose-MSC were placed in hypoxia chambers for 24, 48 and 72 hr at 0.1, 3, 5 and 21% $O_2$ and the release of VEGF was quantified by ELISA testing.

Optimalization of Multi-Dimensional Structure with Demineralised Bone Matrix

AMSCs were induced to undergo osteogenesis by supplementing the MP with Foetal Bovine Serum (FBS, 10% v/v), dexamethasone (1 µM), sodium ascorbate (50 µg/ml), sodium dihydrophosphate and penicillin 100 U/ml and streptomycin 100 µg/ml. Cells were maintained in osteogenic culture with media replaced every 2 days (Post et Al. Bone 2008, 43, 1; 32-39, Qu et Al In Vitro Cell. Dev. Biol. Anim. 2007; 43; 95-100). Cultures were rinsed with PBS and fixed in 70% ethanol and osteogenic differentiation was determined by staining for calcium phosphate with Alizarin red. In addition, immunohistochemistry for osteocalcin and von Kossa stainings were performed to confirm the "bone" phenotype.

A multi-dimensional structure with AMSC was performed with co-incubation in the presence of "Demineralized Bone Matrix (DBM) procured by the University Tissue Bank (University clinical hospital St-Luc, Brussels, Belgium). The production of demineralized bone matrix is disclosed in example 1) Source for Demineralized Bone Matrix The efficacy of DBM is assessed by: (i) the measurement of residual calcium concentration after demineralization process (>97% of [calcium] reduction) and (ii) the in vivo (in nude rats) ostogenic potential at 1 month post-implantation. After an incubation of AMSC (subculture Passage 4) in osteoblastic media during a mean of 15-18 days, different concentration (0/1/5/10 and 20 mg/ml) of DBM is added in the specific differentiation media. The media is replaced every 2 days without removal of DBM. The degree of 3-D structure, the cellular structure, the osteocalcin expression and Von Kossa staining (for calcium deposition) are assessed to select the appropriate DBM concentration for 3-D bone-like structure.

Implantation Procedure and Follow Up of Multi-Dimensional Structure with Demineralised Bone Matrix and AMSCs AMSCs issued from the osteogenic cultures (at passage 4) with optimal DBM concentration (for multi-dimensional structure) were collected for implantation.

Nude rats (Charles River Laboratories International, Inc., Wilmington, Mass., USA) were used as recipients. Cells were implanted in the paraspinal muscles. A longitudinal incision centred on the spine was performed and the sub cutaneous tissues were dissected to expose the fascia. Multi-dimensional structure were directly (University Tissue Bank, Université Catholique de Louvain, Brussels, Belgium) implanted in the para-vertebral musculature. Control was ensured by implanting lyophilized cancellous bone alone in the contro lateral para spinal muscles of the same rat. The fascia was closed using non resorbable suture to allow easy recovery of the implantation site. The animals were sacrificed and explantation was performed at day 30 post-transplantation by the mean of a T61 intracardiac injection (Intervet Int. GmbH-D, Germany) under general anesthesia. The implants were then harvested and processed for histology and micro computed tomography.

Pig recipient. The grafts are tested in two different surgical models. The inventors analyze: (i) their bridging capacity in a femoral cortical bone defect and (ii) their fusion potential in an anterior lumbar interbody fusion (ALIF).

(i) The cortical bone defect model is well known in experimental orthopedic surgery and in our laboratory mainly through the work of Professor C. Delloye. Pigs are used in similar models where a segmental diaphysial bone defect is created on a long bone and then filled with graft material or left empty. In our experiment, both femurs of the pig are operated on. A 1.5-cm cortical bone defect is made and stabilized by a standard 4.5-mm titanium locking compression plate. One femoral defect is left empty and the AMSC graft is implanted into the contralateral leg.

(ii) The ALIF model is well established in porcine experimental surgery. Our technique consists of a four-level ALIF procedure by a posterolateral approach. Fusion is obtained by means of an interbody polyethylethylketone (PEEK) cage. The intervertebral disk is opened and the nucleus pulposus removed, cartilage is reamed to expose the subchondral bone, and the PEEK cage is then inserted. These cages are designed empty but can be filled with various experimental materials. In this case, each level will receive a different graft tissue, creating four different groups: one cage is left empty as the negative control, one cage is filled with freeze-dried irradiated cancellous bone (as often practiced in the clinical field), one cage contains autologous cancellous bone graft (considered as gold standard in fusion procedure and therefore our positive control), and the last cage has the AMSC graft. The animals were sacrificed and explantation was performed at week 7 post-transplantation by the mean of a T61 intracardiac injection (Intervet Int. GmbH-D, Germany) under general anesthesia. The implants were then harvested and processed for histology and computed tomography.

Follow-Up

Nude Rats:

Explanted implants were decalcified in HCl, processed, embedded in parrafin and sectioned (5 μm). Standard coloration by Hemalun Eosin, Masson's Green Trichrom, Osteocalcin and Von Kossa staining were used for histologic staining. Osteocalcin staining were obtained by the means of a monoclonal antibody (OC4-30, Abcam, Cambrige) revealed by the Envision Rsystem monoclonal antibody (Dako, Denmark). The microstructure of the harvested implants was analysed using a pQCT (Peripheral quantitative computed tomography machine, model XCT Research SA, Stratec, Pforzheim, Germany). Cortical and total bone density was measured on multiple slides of each implant. Quantification of in vivo neo-angiogenesis was performed by the quantification of newly-formed vessels after von Willebrandt staining (see above).

Pigs:

The pigs are housed individually with free access to food and water. Postoperative care and analgesia are provided following standard protocols for experimental animal care. In the autograft model, biologic follow-up will consist of inflammation assessment by means of blood samples.

Radiologic follow-up allows us to compare in vivo bone formation by computed tomography (CT) scanning at 1, 5 and 7 weeks post-implantation. The high resolution and multiplanar reconstructions of clinical CT scans are so precise that the inventors can analyze the content of the PEEK cages in vivo, thus allowing evaluation of the fusion process.

The same procedure is used on the femurs, with all information gathered through one scan sweep. An even better resolution is obtained after euthanasia by processing the explanted grafts through micro-CT. Histologic and immunohistochemical investigations on explanted grafts are in progress to assess the new bone formation and the graft revascularization (vascular endothelial growth factor, CD51, von Willebrand factor), consolidation (osteocalcin), and mineralization (von Kossa) compared to the natural cortical bridging and fusion abilities.

The decalcification process allows histologic and immunohistochemical studies of the grafted material. Histology, histomorphometry, and microradiography require keeping the tissue calcified; thus, non-decalcified processing is also mandatory.

Statistics

The statistical significance of differences between groups was tested by one-way analysis of variance with a Bonferroni's post hoc test. The statistical tests were carried out with Systat version 8.0. Differences were considered to be significant at $p<0.05$.

Results

Proof of Concept for Multi-Dimensional Structure with Optimal DBM Concentration: In Vitro Bone-Like Structure In view to avoid a biological support for AMSC cell transplantation, a multi-dimensional structure was developed in combination with DBM. Demineralized Bone Matrix (with a mean diameter of 700 μm) with an in vivo capacity to promote Osteogenic differentiation in nude rats (Quality control required prior using in contact with AMSCs), is required to achieve an in vitro cellular remodelling in co-incubation with AMSCs.

In both osteogenic differentiation media, supplemented-DBM induced the development of a tri-dimensional structure by a cellular constriction, collagen synthesis and regroupment of DBM particles in comparison with AMSCs alone without DBM. In view to optimise the development of multidimensional structure, gradual DBM doses were tested. Extreme concentrations (more than 20 mg/ml) were found to be not adapted. 1 mg/ml did not developed an optimal 3-D structure for graft handling in view to surgical application. In contrast, 5 and 10 mg/ml were found to develop an optimal tissue retraction for graft removal and surgical application. Microscopically, osteocalcin expression and mineralization process (Von Kossa staining) were revealed with these latest DBM concentration. A mean of 20±3 days of co-incubation with DBM is required to obtain a tri-dimensional structure with AMSCs in osteogenic conditions.

Proof of Concept for Multi-Dimensional Structure with Optimal DBM Concentration: In Vivo Osteogenesis Nude Rats After 30 days post-implantation in nude rats, AMSCs alone without DBM did not induced the formation a new bone-like structure. Only small bone nodules (osteocalcin +) as stained by Von Kossa were sparsely distributed in nude rats musculature. In contrast, the implantation of the multi-dimensional structure was easily performed with a good localization of implantation site. After 30 days post-implantation, a compact/strong bone-like structure was found into the muscle with a microscopically dense connective tissue within DBM particle. A bone-like structure was found with osteocalcin staining connective tissue and mineralization process.

Pig Recipients

After 5 weeks post-implantation, in pig, no spontaneous consolidation was found in bone femoral defect (with no-treatment) as revealed by CT-scan. It was easy to incorporate the multi-dimensional structure in the bone defect without any scaffold. This latest graft significantly improve the bone consolidation at early period post-implantation (5 weeks post-transplantation) with bone-like structure bridging the native cortical bone defect.

Proof of Concept for Multi-Dimensional Structure with Optimal DBM Concentration: In Vivo Angiogenesis To assess in vitro the proangiogenic capacities of stem cells in normoxic and hypoxic conditions, pre-clinical porcine Bone Marrow-MSC and Adipose MSC were placed in hypoxia chambers for 24, 48 and 72 hr at 0.1, 3, 5 and 21% $O_2$ and the release of VEGF was quantified by ELISA. BM-MSC released more VEGF in hypoxia than in normoxic conditions and maintained this secretion in the time with higher levels of VEGF at 48 and 72 hr than at 24 hr ($p<0.05$).

Figure 6:
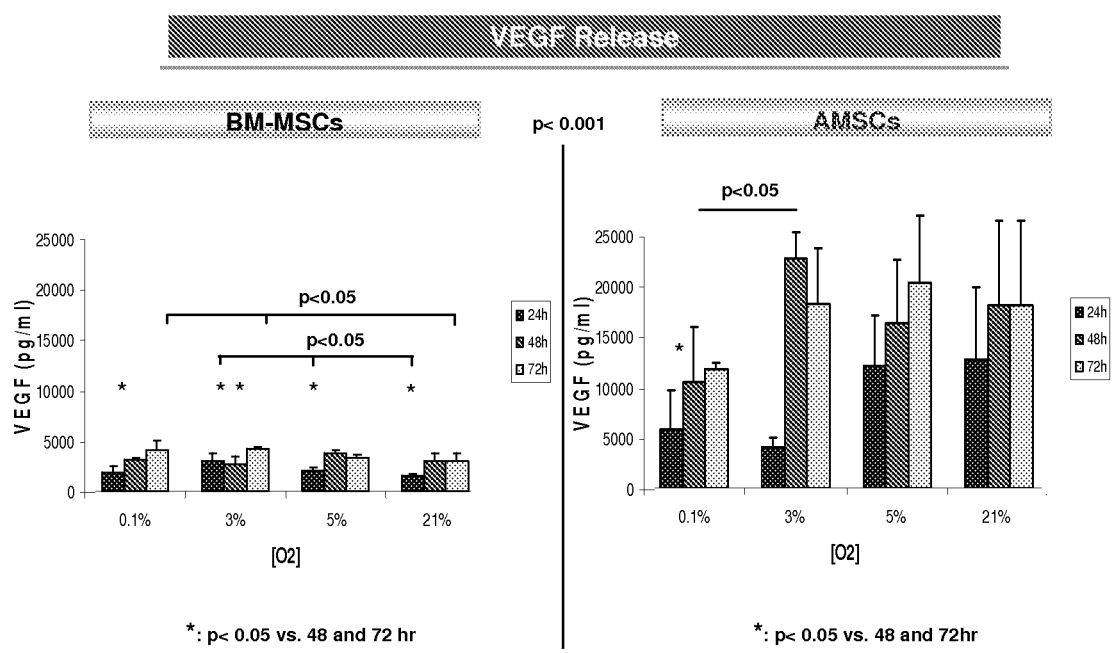
FIG. 6 shows the angiogenic potential of AMSCs versus BM-MSCs. In vitro potential was found by incubation of both cells at different Oxygen concentrations (0.1, 3, 5 and 21% O2). AMSCs demonstrated, at each O2 concentrations, a significant higher release of VEGF than BM-MSCs.

In contrast, VEGF release from AMSC was similar in the different culture conditions but significant higher levels of VEGF were released by AMSC than BM-MSC (11274±679 vs. 2364±94 pg/ml, respectively; p<0.05) (FIG. 6).

These results were confirmed in vivo after transplantation of BM-MSC and AMSC. A significant higher angiogenesis was found in case of osteogenic AMSCs transplantation in comparison to BM-MSCs (p<0.05).

The invention claimed is:

1. A biomaterial having a multi-dimensional structure and comprising a differentiated mesenchymal stem cells (MSCs) tissue containing osteocalcin-expressing cells or proteoglycan-expressing cells, interconnective tissue including collagen and demineralized bone matrix (DBM), wherein said demineralized bone matrix is dispersed within the differentiated MSCs tissue, wherein said MSCs are adipose tissue-derived stem cells, and wherein said biomaterial is capable of secreting vascular endothelial growth factor (VEGF), thereby inducing revascularization in vivo.

2. The biomaterial of claim 1, wherein MSCs are of human or animal origin.

3. The biomaterial of claim 1, wherein the MSCs are late passaged adipose tissue-derived stem cells.

4. The biomaterial of claim 1, further defined as three-dimensional.

5. The biomaterial of claim 1, further comprising osteocytes comprising a mineral coating.

6. The biomaterial of claim 1, further comprising chondrocytes and an extracellular matrix comprising collagen and proteoglycans.

7. The biomaterial of claim 1, wherein the demineralized bone matrix is in the form of particles having a mean diameter of 50-2500 µm.

8. A medical device comprising a biomaterial of claim 1.

9. The medical device of claim 8, which is implantable.

10. The medical device of claim 8, further defined as comprised in a kit.

11. The medical device of claim 8, wherein the kit comprises a suitable fixation means.

12. The biomaterial of claim 1, wherein said adipose-tissue derived stem cells are differentiated prior to be contacted with said DBM.

13. A biomaterial having a multi-dimensional structure and comprising a differentiated mesenchymal stem cells (MSCs) tissue containing osteocalcin-expressing cells or proteoglycan-expressing cells, interconnective tissue including collagen and demineralized bone matrix (DBM), wherein said demineralized bone matrix is dispersed within the differentiated MSCs tissue, wherein said MSCs are adipose tissue-derived stem cells, and wherein said differentiated MSC tissue is capable of secreting vascular endothelial growth factor (VEGF), thereby inducing revascularization in vivo.

* * * * *